United States Patent
Moore et al.

(10) Patent No.: US 7,935,937 B2
(45) Date of Patent: May 3, 2011

(54) METHOD OF FORMING TEM SAMPLE HOLDER

(75) Inventors: Thomas M. Moore, Dallas, TX (US); Gonzalo Amador, Dallas, TX (US); Lyudmila Zaykova-Feldman, Dallas, TX (US)

(73) Assignee: Omniprobe, In.c, Dallas, TX (US)

( * ) Notice: Subject to any disclaimer, the term of this patent is extended or adjusted under 35 U.S.C. 154(b) by 248 days.

(21) Appl. No.: 12/391,552

(22) Filed: Feb. 24, 2009

(65) Prior Publication Data

US 2009/0294690 A1    Dec. 3, 2009

Related U.S. Application Data

(60) Division of application No. 11/433,850, filed on May 12, 2006, now abandoned, which is a continuation-in-part of application No. 10/896,596, filed on Jul. 22, 2004, now Pat. No. 7,053,383.

(60) Provisional application No. 60/519,046, filed on Nov. 11, 2003.

(51) Int. Cl.
  *G01N 23/00* (2006.01)
  *G01F 23/00* (2006.01)
(52) U.S. Cl. ............... 250/442.11; 250/440.11; 250/311
(58) Field of Classification Search .......... 250/306, 250/307, 310, 311, 440.11, 441.11, 442.11
See application file for complete search history.

(56) References Cited

U.S. PATENT DOCUMENTS

| | | | | |
|---|---|---|---|---|
| 6,717,156 | B2* | 4/2004 | Koike et al. | 250/440.11 |
| 7,053,383 | B2* | 5/2006 | Moore | 250/440.11 |
| 7,115,882 | B2* | 10/2006 | Moore | 250/440.11 |
| 7,126,132 | B2* | 10/2006 | Moore | 250/440.11 |
| 7,126,133 | B2* | 10/2006 | Moore | 250/440.11 |
| 7,315,023 | B2* | 1/2008 | Moore | 250/311 |
| 7,381,971 | B2* | 6/2008 | Moore et al. | 250/442.11 |
| 7,395,727 | B2* | 7/2008 | Moore | 73/866.5 |
| 7,414,252 | B2* | 8/2008 | Moore et al. | 250/492.21 |
| 7,423,263 | B2* | 9/2008 | Hong et al. | 250/304 |
| 7,834,315 | B2* | 11/2010 | Zaykova-Feldman et al. | 250/307 |
| 2002/0166976 | A1* | 11/2002 | Sugaya et al. | 250/440.11 |
| 2006/0219919 | A1* | 10/2006 | Moore et al. | 250/311 |
| 2009/0320624 | A1* | 12/2009 | Amador | 73/866.5 |
| 2010/0305747 | A1* | 12/2010 | Agorio et al. | 700/213 |

* cited by examiner

*Primary Examiner* — Bernard E Souw
(74) *Attorney, Agent, or Firm* — John A. Thomas (57) ABSTRACT

A TEM sample holder is formed from at least one nano-manipulator probe tip and a TEM sample holder pre-form. The probe tip is permanently attached to the TEM sample-holder pre-form to create a TEM sample holder before attachment of a sample to the point of the probe tip inside a FIB. In the preferred embodiment the probe tip is attached to the TEM sample holder pre-form by applying pressure to the pre-form and the probe tip, so as to cause plastic flow of the pre-form material about the probe tip. The TEM sample holder may have smaller dimensions than the TEM sample holder pre-form; in this case the TEM sample holder is cut from the larger TEM sample holder pre-form, preferably in the same operation as attaching the probe tip.

30 Claims, 7 Drawing Sheets

METHOD OF FORMING TEM SAMPLE HOLDER

CLAIM FOR PRIORITY AND INCORPORATION BY REFERENCE

This is a divisional application of continuation-in-part patent application Ser. No. 11/433,850, filed May 12, 2008, which continuation-in-part application claims the priority of application Ser. No. 10/896,596, filed Jul. 22, 2004, further claiming priority from U.S. provisional patent application No. 60/519,046, filed Nov. 11, 2003. Continuation-in-part application Ser. No. 11/433,850 and application Ser. No. 10/896,596 are incorporated into this divisional application by reference.

BACKGROUND

1. Technical Field

This disclosure relates to the use of focused ion-beam (FIB) microscopes for the preparation of specimens for later analysis in the transmission electron microscope (TEM), and apparatus and methods to facilitate these activities.

2. Background Art

The use of focused ion-beam (FIB) microscopes has become common for the preparation of specimens for later analysis in the transmission electron microscope (TEM). The structural artifacts, and even some structural layers, in the device region and interconnect stack of current integrated-circuit devices can be too small to be reliably detected with the secondary electron imaging in a Scanning Electron Microscope (SEM), or FIB, which offers a bulk surface imaging resolution of approximately 3 mm. In comparison, TEM inspection offers much finer image resolution (<0.1 nm), but requires electron-transparent (<100 nm thick) sections of the sample mounted on 3 mm diameter grid disks.

Techniques were later developed for cutting out and removing specimens for examination that required little or no preliminary mechanical preparation of the initial semiconductor die sample before preparation in the FIB. These lift-out techniques include an "ex-situ" method that is performed outside the FIB chamber, and "in-situ" methods performed inside the FIB.

The conventional process of in-situ lift-out can be simplified into three successive steps. The first is the excision of the sample using focused ion-beam milling and extraction of the sample from its trench. The second is the "holder-attach" step, during which the sample is translated on the probe-tip point to the TEM sample holder. Then it is attached to the TEM sample holder (typically with ion beam-induced metal deposition) and later detached from the probe-tip point. The third and final step is the thinning of the sample into an electron-transparent thin section using focused ion beam milling.

A significant portion of the total time involved in completing a TEM sample with in-situ lift-out is spent during the holder-attach step. The relative amount of time involved depends on the amount of time required to mechanically isolate the lift-out sample from the initial bulk sample (ion beam milling rate), but will vary between 30% to 60% of the total time for TEM sample preparation. In order to eliminate the holder-attach step, it would be desirable to directly join the probe tip to the material that will form the TEM sample holder, and thereafter attach the excised sample to the probe tip of the newly-formed TEM sample holder. This newly created assembly is robust and easy to pick up with the tweezers, allowing smooth transfer inside and outside the FIB without the necessity to vent the FIB vacuum chamber.

DESCRIPTION

The preferred embodiment includes a novel method and apparatus for joining a nano-manipulator probe tip (150) to a solid piece of material comprising a TEM sample holder pre-form (100). In the preferred embodiment, this mechanical process is performed outside the vacuum chamber, although it could be performed inside the FIB 23 chamber as well. In the preferred embodiment, the step of embedding a probe tip (150) into the TEM sample holder pre-form (100) is completed outside the FIB, using the mechanical press described in the U.S. patent application Ser. No. 10/896,596. In the present disclosure, however, the TEM sample holder (210) with the probe tip (150) attached is formed before the attachment of an excised sample to the probe tip point (160), rather than afterwards.

The assembly comprising the probe tip (150) attached to a TEM sample holder pre-form (100), can be picked up by the tweezers or grippers (350) and then transferred into the FIB for the in-situ lift-out procedure or for other purposes. This transfer can be accomplished by several means, including but not limited to, the transfer of the assembled TEM sample holder (210) through the sample door of a FIB equipped with a door, translation of the TEM sample holder (210) through a vacuum airlock on the nano-manipulator device, or the translation of the sample holder (210) in a cassette that passes through a vacuum airlock on the FIB chamber. All but the first means listed do not require that the FIB vacuum chamber be vented to atmosphere, which offers cycle time reduction and long-term equipment reliability advantages.

The TEM Sample Holder Pre-Form

Figure 1:
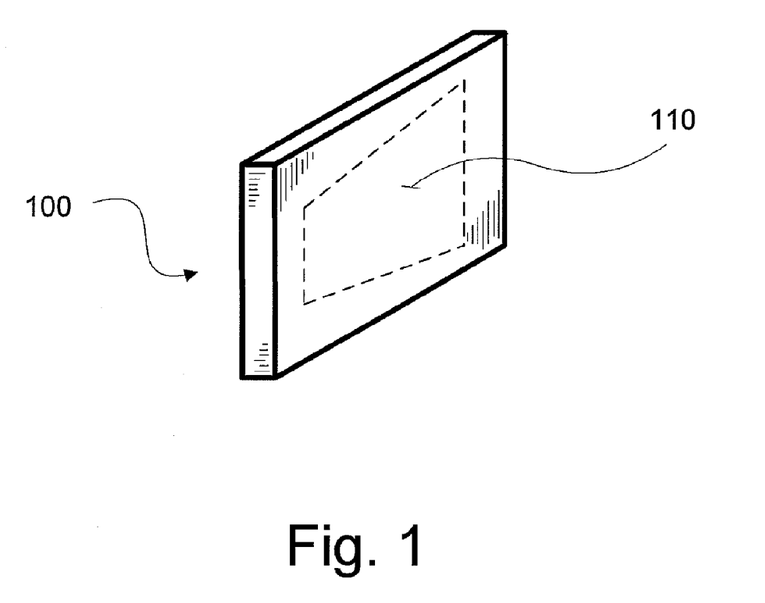
FIG. 1 is a perspective view of a typical TEM sample pre-form, in rectangular shape, also showing the shape of a TEM sample holder therein.
Figure 2:
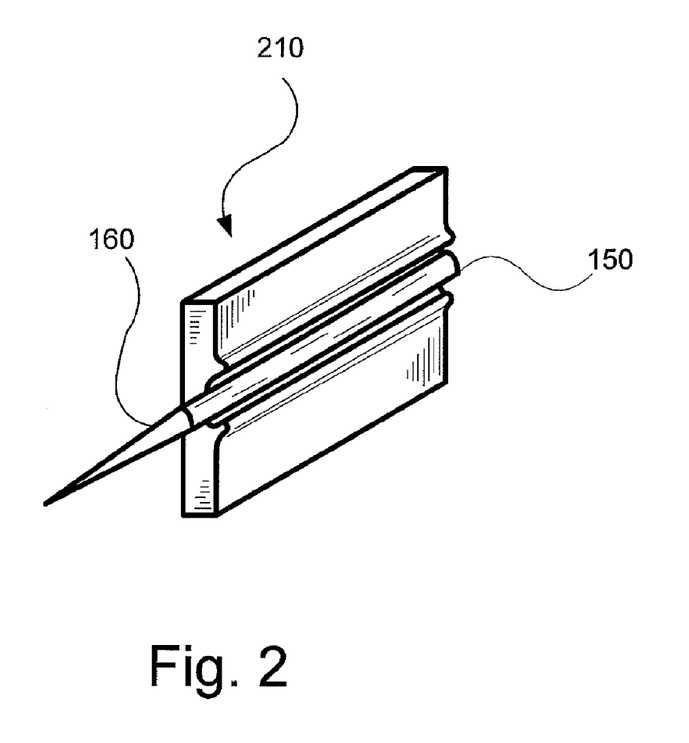
FIG. 2 is a perspective view of a probe tip embedded into a TEM sample pre-form having a rectangular shape.
Figure 3:
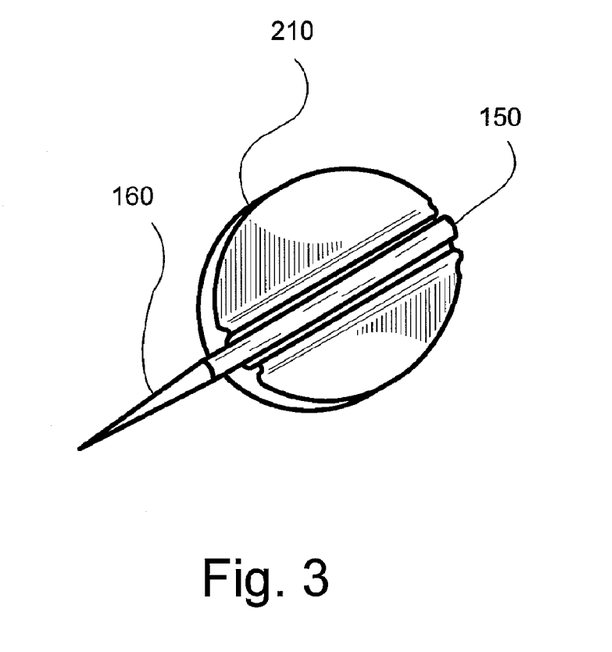
FIG. 3 is a perspective view of a probe tip embedded into a TEM sample pre-form having a circular shape.
Figure 4:
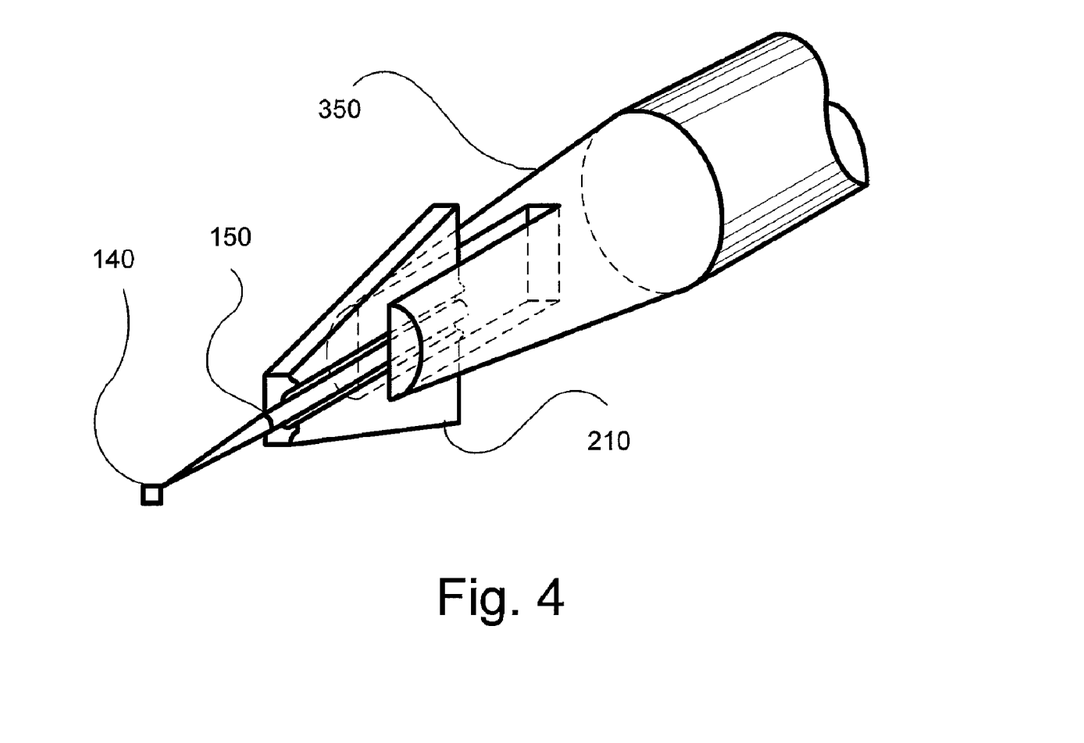
FIG. 4 is a perspective view of a probe tip embedded into a TEM sample pre-form having a pennant-like shape, picked up by the grippers.

In the preferred embodiment, the probe tip (150) is attached to a TEM sample holder pre-form (100) by a combined mechanical forming and cutting operation, as described in U.S. patent application Ser. No. 10/896,596. As shown in FIG. 1, the TEM sample holder pre-form (100) is a sheet of material of approximately the same thickness as a standard TEM grid. In the preferred embodiment, this sheet of material can be of any suitable geometrical shape, but preferably it is of rectangular shape, as shown in FIG. 1, a circular shape as shown in FIG. 3, or a pennant-like shape, as shown in FIG. 4. One of such shapes could be cut from the other during the combined mechanical forming and cutting operation, as described in the incorporated application, where the TEM sample holder pre-form (100) is referred to as a "coupon." This new assembly (210), shown in FIGS. 2-4, can be easily picked up using grippers or tweezers (350) and transferred into the FIB for an attachment of a lift-out sample (140), or placed into a standard cassette. FIG. 1 shows how, in some embodiments, the resulting shape (110) of the TEM sample holder (210) is cut from the sample holder pre-form in the attachment step, described below. In other embodiments, the shape of the pre-form (100) is the final shape of the assembled TEM sample holder (210).

The probe tip (150) can be joined to the material that will form the TEM sample holder pre-form (100), so as to preserve the attachment between the probe tip (150) and this material, and prevent the probe tip (150) from separating from the TEM sample holder pre-form material (100) during transportation, storage or inspection in the TEM. The assembly should not interfere with the normal operation of the FIB, TEM, or other intended analytical instrument, and should survive well in the internal environment of the TEM, or other intended analytical instrument.

The TEM sample holder pre-form (100) material is preferably soft copper, but may also be molybdenum, aluminum, gold, silver, nickel, beryllium, or copper coated with such metals, if appropriate to the application. FIGS. 2-4 show a nano-manipulator probe tip (150) placed across the TEM sample holder pre-form (100). The probe tip (150) has a probe-tip point (160) that holds a sample (140) for analysis. Typically, the probe-tip point (160) is a fine tungsten needle.

The TEM sample holder pre-form (100) may also be fabricated from a material harder than copper, such as molybdenum, or it may have a surface structure that facilitates the mechanical embedding of the probe tip (150) in the TEM sample holder pre-form (100) material, illustrated in FIGS. 11 and 12 and discussed below.

Excess parts of the TEM sample holder pre-form material (100), if any, are severed during the combined mechanical forming and cutting operation, described in the U.S. patent application Ser. No. 10/896,596. In addition, the probe tip (150) is cut off substantially at the edge of the finished TEM sample holder (210).

Methods of Attaching the Probe Tip to the Tem Sample Holder Pre-Form

Figure 5:
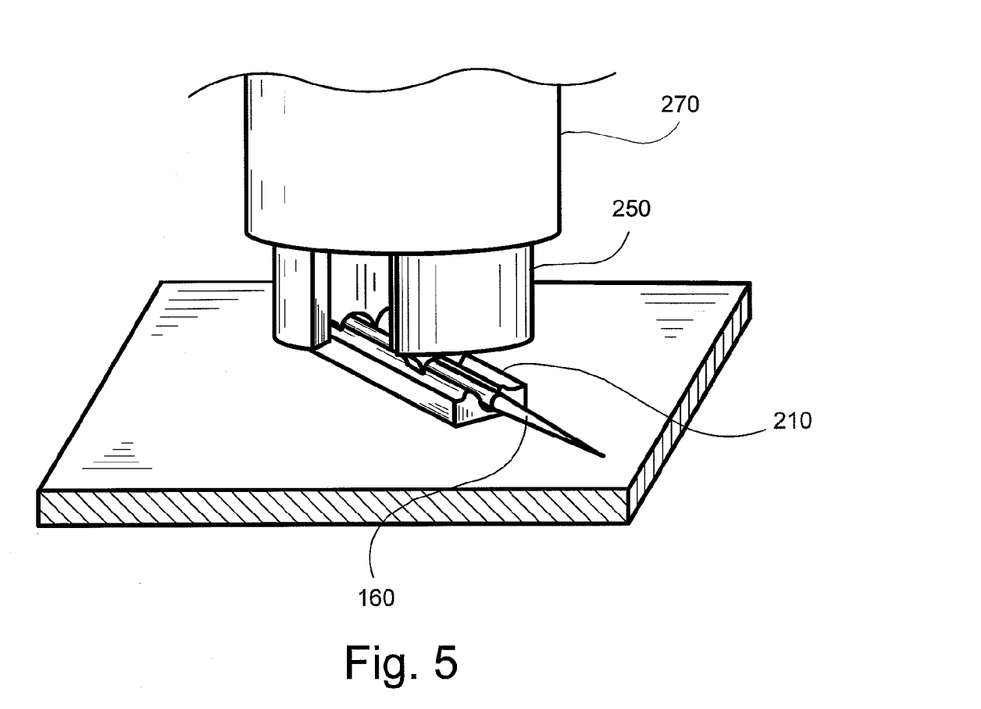
FIG. 5 is a perspective view of the shear punch of a press, shown having engaged a probe tip embedded into a TEM sample pre-form of rectangular shape, located on the press platform.
Figure 6:
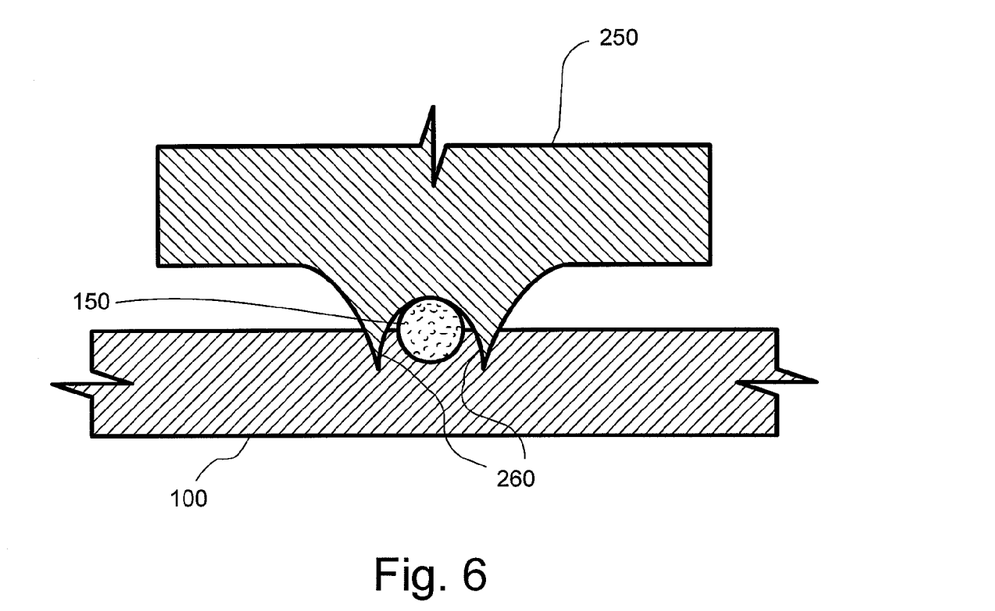
FIG. 6 is a cross-sectional view of a probe tip positioned in a press and engaged by the former rod of the press.
Figure 7:
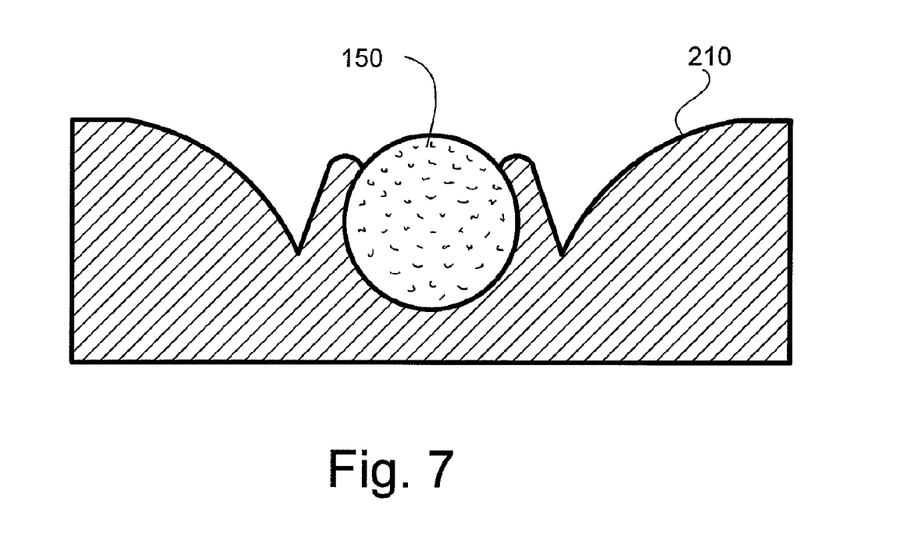
FIG. 7 is a cross-sectional view of a probe tip embedded in the material of a TEM sample pre-form.

FIGS. 5-12 show methods for joining the probe tip (150) to the TEM pre-form (100). FIG. 6 is a view of mechanical deformation of the material of the TEM sample holder pre-form material (100) or probe tip (150), or both, to embed the probe tip (150) into the material of the TEM sample pre-form. FIG. 5 shows the press previously described acting to embed a probe tip (150) into a TEM sample holder pre-form (100) to form the completed sample holder (210). The shear punch (270) moves downward carrying a former rod (250) that impacts the pre-form (100) and the probe tip (150). As shown in FIG. 6, the former rod (250) presses the probe tip (150) into the pre-form material (100), preferably assisted with teeth (260) on the former rod (250) for holding the probe tip (150) and flowing the pre-form (100) material around it. FIGS. 6 and 7 show a cross-section of this operation and result. Excess parts of the TEM sample holder pre-form material (100), if any, are severed during the combined mechanical forming and cutting operation. In addition, the probe tip (150) is cut off substantially at the edge of the finished TEM sample holder (210).

Figure 8:
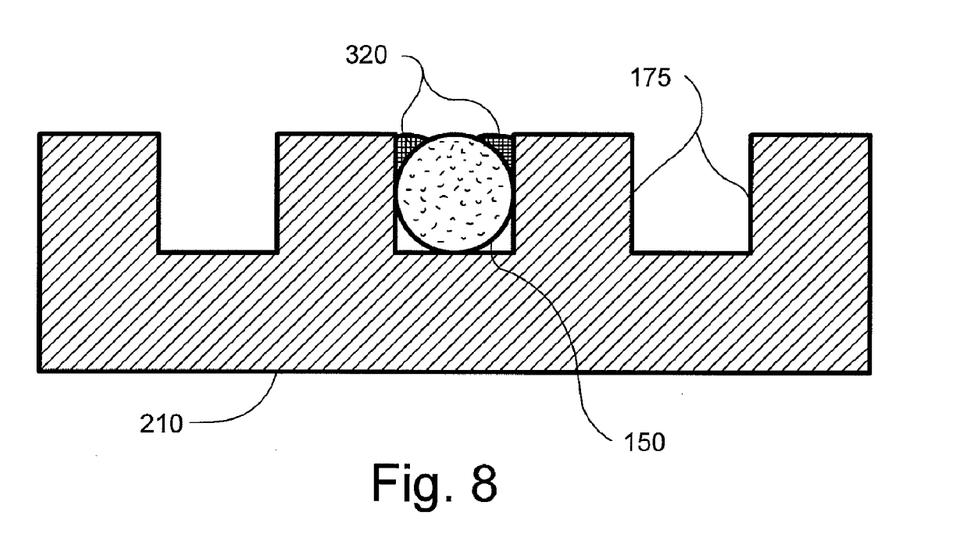
FIG. 8 is a cross-sectional view of a probe tip attached to a corrugated material with electrical or thermal bonding.
Figure 9:
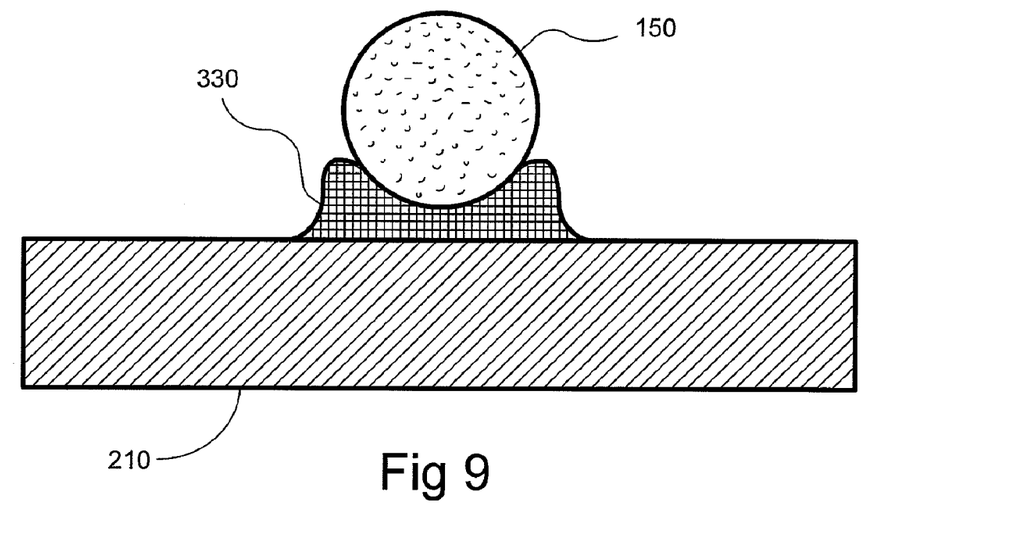
FIG. 9 is a cross-sectional view of a probe tip attached to the material using an adhesive.
Figure 10:
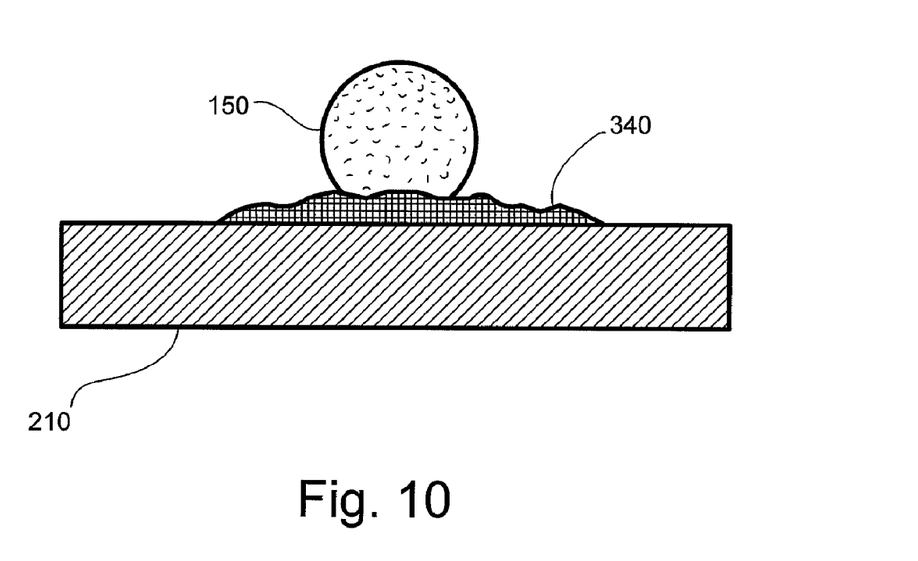
FIG. 10 is a cross-sectional view of the probe tip bonded to the TEM sample pre-form with CVD or an evaporated material.

FIG. 8 depicts electrical or thermal bonding (320), such as welding, of the probe tip (150) to the TEM sample holder pre-form material (100). FIG. 8 also shows corrugations (175) in the TEM sample holder pre-form material. FIG. 9 shows bonding the probe tip (150) to the TEM sample holder pre-form material (100) with a suitable glue or adhesive (330). FIG. 10 shows bonding the probe tip (150) to the TEM sample holder pre-form material (100) with a CVD or evaporated material (340).

Figure 11:
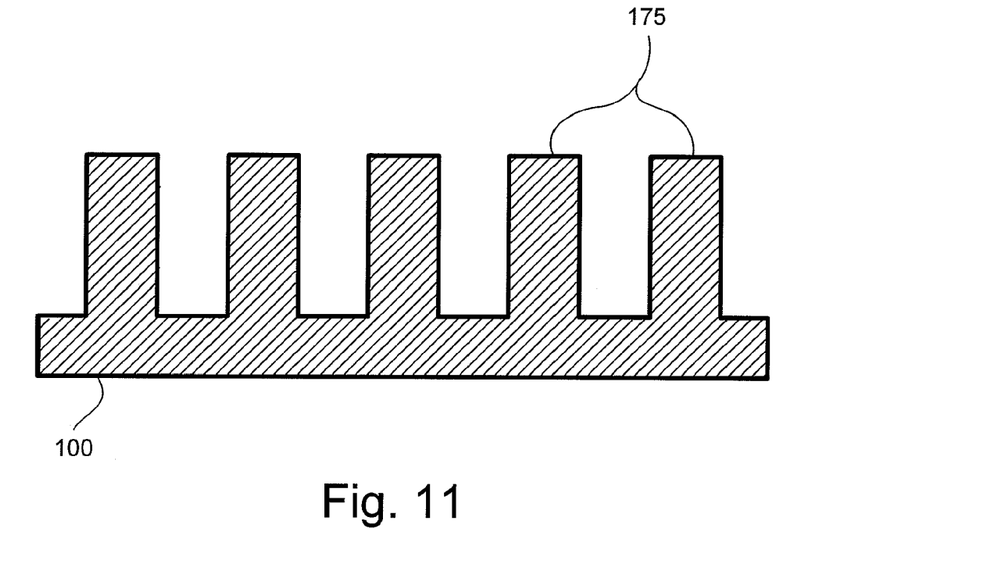
FIG. 11 is a transverse view of a corrugated material.
Figure 12:
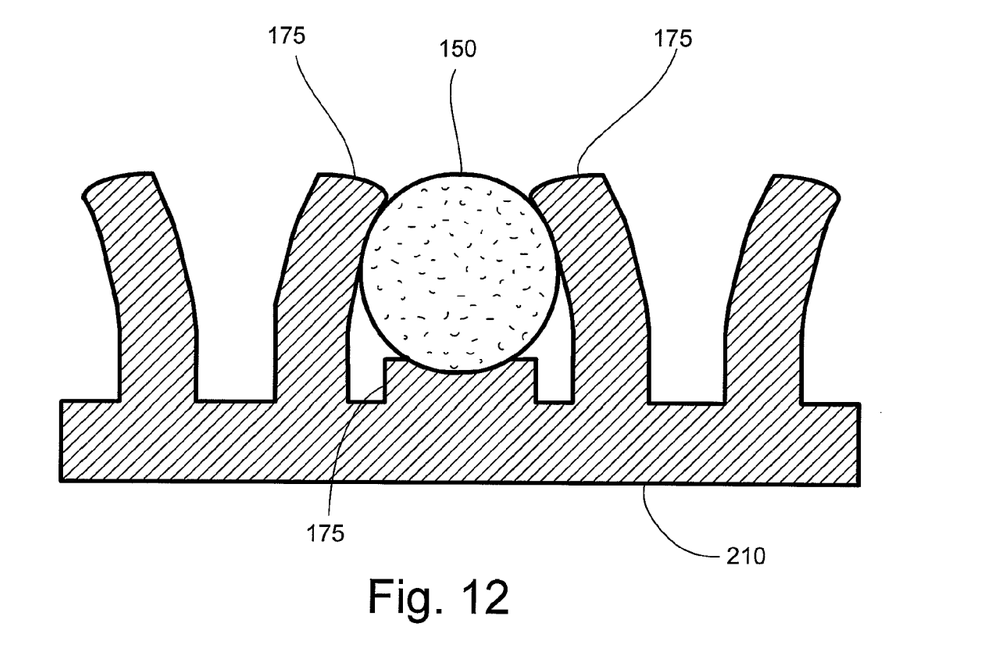
FIG. 12 is a transverse view of a probe tip, embedded into a corrugated material.

FIGS. 11 and 12 show cross-sections of a corrugated structure with corrugations (175) having a period approximately the same or less than the probe tip (150) diameter. In FIG. 11, the corrugation period is about half the diameter of the probe tip (150). The corrugations (175) may be periodic, such as continuous rows or ridges roughly aligned in the direction of the probe tip, rows of individual posts, or non-periodic free-form elevations. These structures can be easily deformed to lock the probe tip (150) in place.

Once the assembly of the TEM sample holder pre-form material (100) with the probe tip (150) attached to it has been created, it can be picked up by the grippers or tweezers (350) (shown in FIG. 4) and transferred to the FIB for the in-situ lift-out operation. The in-situ lift-out process can be followed with the final thinning operation, during which the desired portion of the lift-out sample (140) or samples is thinned to electron transparency (typically 50-250 nm). This final thinning can be performed in an off-line FIB to maximize throughput of the in-line FIB and to take advantage of the efficiency, expertise and dedicated resources of the off-line FIB lab that can be located outside the clean room. However, if the apparatus for attaching the probe tip (150) to a TEM sample holder pre-form (100) is located inside the FIB, the final thinning operation can be performed immediately after the in-situ lift-out operation. This process is shown as a flowchart in FIG. 13.

Figure 13:
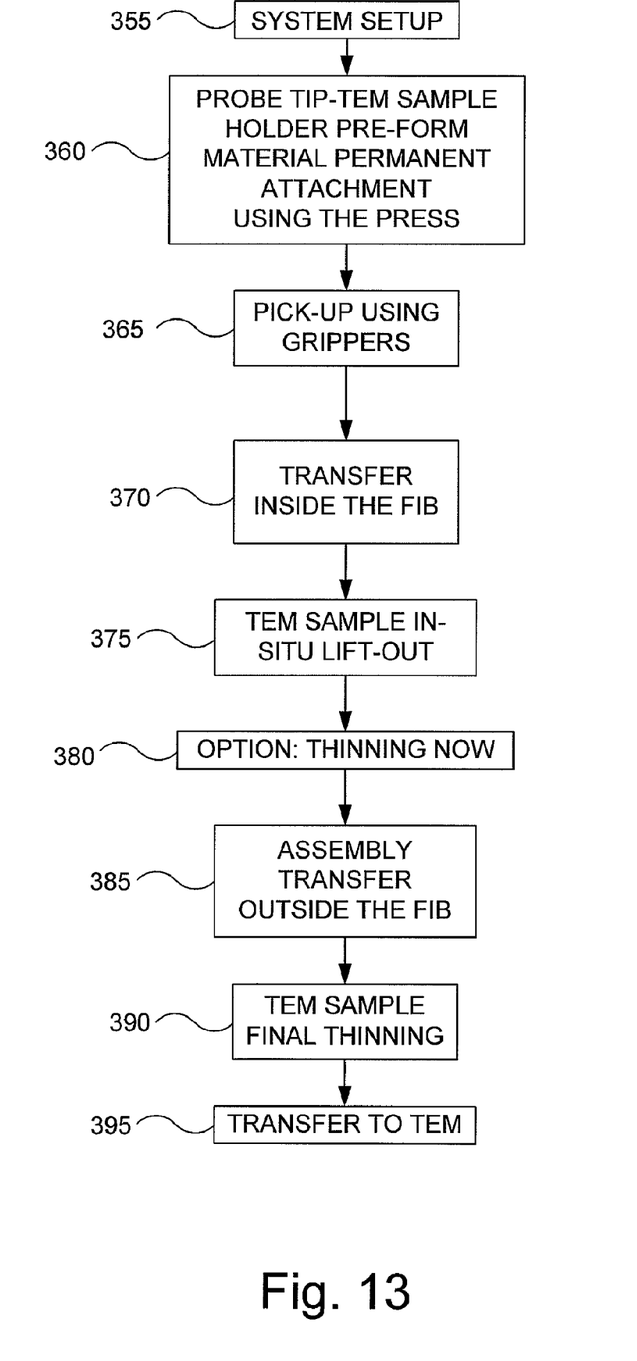
FIG. 13 is a flowchart showing the operational sequence of a preferred embodiment.

After initial system setup in step 355, the probe tip (150) and the TEM sample pre-form (100) are permanently attached in step 360, using the press as described above, forming the TEM sample holder (210). The completed sample holder (210) is grasped by grippers (350) in step 365 and transferred into the FIB chamber in step 370. Inside the FIB, in step 375, the in-situ lift-out of the sample of interest (140) is performed, including the attachment of the sample (140) to the probe tip point (160). At step 380 the sample (140) may optionally be thinned before transfer outside the FIB. At step 385 the sample holder (210) bearing the attached sample (140) is removed from the FIB, optionally for final thinning at step (390). Finally, at step 395, the sample holder (210) with the attached sample (140) is transferred to a TEM or other instrument for inspection.

Since those skilled in the art can modify the specific embodiments described above, we intend that the claims be interpreted to cover such modifications and equivalents.

We claim:

1. A method of preparing a sample for examination in a TEM, the method comprising:
joining at least one probe tip to a TEM sample holder pre-form;
forming a TEM sample holder from the probe tip and the TEM sample holder pre-form; and, thereafter,
attaching a sample to the point of a probe tip.

2. The method of claim 1 where the probe tip is joined to the TEM sample holder pre-form outside a FIB vacuum chamber.

3. The method of claim 1 where the probe tip is joined to the TEM sample holder inside a FIB vacuum chamber.

4. A method of preparing a sample for examination in a TEM; the method comprising:
providing a TEM sample holder pre-form;
providing at least one probe tip; the probe tip having a point;
embedding the probe tip in the TEM sample holder form;
cutting off that portion of the probe tip outside the boundary of the TEM sample holder form;
cutting the TEM sample holder free from the TEM sample holder pre-form; and,
thereafter, attaching a sample to the probe-tip point.

5. The method of claim 4 where the step of embedding further comprises applying pressure to the TEM sample holder and the probe tips so as to cause plastic flow of the TEM sample holder material about the probe tips.

6. The method of claim 1 where the step of joining further comprises welding the probe tip to the TEM sample holder.

7. The method of claim 1 where the step of joining further comprises attaching the probe-tip to the TEM sample holder with adhesive.

8. The method of claim 1 where the step of joining further comprises attaching the probe tip to the TEM sample holder by chemical-vapor deposition.

9. The method of claim 4 where the steps of cutting off of the portion of the probe tip outside the TEM sample holder boundary and the cutting free of a TEM sample holder are simultaneous.

10. A method of preparing a sample for examination in a TEM, the method comprising:
providing a TEM sample holder pre-form;
providing a probe tip; the probe tip having a point;
forming a TEM sample holder from the probe-tip and the TEM sample holder pre-form outside a FIB; and, thereafter,
excising a sample from a substrate inside the FIB;
attaching the sample to the probe-tip point inside the FIB;
removing the probe-tip point and the sample attached to it from the FIB.

11. The method of claim 10, where the step of forming a TEM sample holder further comprises:
providing a TEM sample holder form in the TEM sample holder pre-form;
embedding the probe-tip point in the TEM sample holder form;
cutting off that portion of the probe-tip point outside the TEM sample holder form outer boundary; and,
cutting the TEM sample holder form free from the TEM sample holder pre-form.

12. The method of claim 11, where the step of embedding further comprises applying pressure to the TEM sample holder and the probe-tip so as to cause plastic flow of the TEM sample holder material about the probe-tip.

13. The method of claim 10, where the step of forming comprises welding the probe-tip point to the TEM sample holder.

14. The method of claim 10, where the step of forming comprises attaching the probe-tip point to the TEM sample holder with adhesive.

15. The method of claim 10, where the step of forming comprises attaching the probe tip to the TEM sample holder by chemical-vapor deposition.

16. The method of claim 11 where the cutting off of the portion of the probe tip outside the TEM sample holder boundary and the cutting free of a TEM sample holder are simultaneous.

17. The method of claim 10 further comprising returning the sample to the FIB for further thinning after forming the TEM sample holder.

18. A method of preparing a sample for examination in a TEM, the method comprising:
providing at least one probe tip; the probe tip having a probe-tip point;
joining the probe-tip to a TEM sample holder pre-form inside the FIB;
forming a TEM sample holder from the probe-tip and the TEM sample holder pre-form inside the FIB vacuum chamber.
excising a sample from a substrate inside a FIB; and,
attaching the sample to the probe-tip point inside the FIB.

19. The method of claim 18, where the step of joining the probe tip to the TEM sample holder pre-form and forming a TEM sample holder further comprises:
providing a TEM sample holder form in the TEM sample holder pre-form;
embedding the probe tip in the TEM sample holder form;
cutting off that portion of the probe tip outside the TEM sample holder form outer boundary; and,
cutting a TEM sample holder free from the TEM sample holder pre-form.

20. The method of claim 19, where the step of embedding further comprises applying pressure to the TEM sample holder and the probe tip so as to cause plastic flow of the TEM sample holder material about the probe tip.

21. The method of claim 19, where the step of joining further comprises welding the probe tip to the TEM sample holder.

22. The method of claim 19, where the step of joining further comprises attaching the probe tip to the TEM sample holder with adhesive.

23. The method of claim 19, where the step of joining further comprises attaching the probe tip to the TEM sample holder by chemical-vapor deposition.

24. The method of claim 19 where the cutting off of the portion of the probe tip outside the TEM sample holder boundary and the cutting free of a TEM sample holder are simultaneous.

25. The method of claim 19 where step of joining further comprises:
providing corrugations on at least the surface of the TEM sample holder pre-form comprising the TEM sample holder form;
where the corrugations have a period approximately equal to or less than the diameter of the probe tip.

26. The method of claim 25 where the period of the corrugations varies randomly.

27. The method of claim 25 where the corrugations comprise rows of posts.

28. The method of claim 19 where step of joining further comprises:
providing corrugations on at least the surface of the TEM sample holder pre-form comprising the TEM sample holder form;

where the corrugations have a period approximately equal to or less than the diameter of the probe tip.

29. The method of claim 19 where the period of the corrugations varies randomly.

30. The method of claim 19 where the corrugations comprise rows of posts.

* * * * *